(12) United States Patent
Las Navas Garcia

(10) Patent No.: US 10,267,719 B2
(45) Date of Patent: Apr. 23, 2019

(54) METHOD FOR AUTOMATIC THERMOGRAVIMETRIC VOLATILE ANALYSIS OF COAL AND COKE

(71) Applicant: Jose Maria Las Navas Garcia, Conway, SC (US)

(72) Inventor: Jose Maria Las Navas Garcia, Conway, SC (US)

( * ) Notice: Subject to any disclaimer, the term of this patent is extended or adjusted under 35 U.S.C. 154(b) by 127 days.

(21) Appl. No.: 15/494,912

(22) Filed: Apr. 24, 2017

(65) Prior Publication Data

US 2018/0306692 A1 Oct. 25, 2018

(51) Int. Cl.
| G01N 25/00 | (2006.01) |
| G01K 1/00 | (2006.01) |
| G01K 17/00 | (2006.01) |
| G01N 5/04 | (2006.01) |
| G01N 33/22 | (2006.01) |
| G01G 1/00 | (2006.01) |

(52) U.S. Cl.
CPC ............... G01N 5/04 (2013.01); G01G 1/00 (2013.01); G01N 25/00 (2013.01); G01N 33/222 (2013.01)

(58) Field of Classification Search
USPC .......................................... 374/14, 208, 31
See application file for complete search history.

(56) References Cited

U.S. PATENT DOCUMENTS

| 4,388,410 A | 6/1983 | Arroyo et al. |
| 4,824,790 A | 4/1989 | Carangelo et al. |
| 5,207,507 A | 5/1993 | Kimoto et al. |
| 6,074,205 A | 6/2000 | Myburgh |
| 7,404,670 B2 * | 7/2008 | Willis .................... F27B 14/00 219/483 |
| 9,249,357 B2 | 2/2016 | Quanci et al. |
| 9,377,419 B2 | 6/2016 | Las Navas Garcia |
| 2012/0132472 A1 | 5/2012 | Las Navas Garcia |
| 2014/0105249 A1 * | 4/2014 | Yasutomi ................. G01K 1/08 374/208 |

FOREIGN PATENT DOCUMENTS

WO WO2012031002 3/2012

* cited by examiner

*Primary Examiner* — Mirellys Jagan
(74) *Attorney, Agent, or Firm* — Ernest Lipscomb; Barnwell Whaley Patterson & Helms, LLC

(57) ABSTRACT

An automatic method for thermogravimetric analysis of multiple samples of coal or coke for volatile matter in a thermogravimetric analyzer of the type including an auto-loading delivery system, a furnace, a movable platform within said furnace, an external balance and an internal balance for measuring the weights of sample holders, lids and samples before and after treatment in the furnace. Coal or coke samples are placed in the sample holders and weighed in the external balance and are auto-loaded into the furnace at 950° C. All sample holders are weighed sequentially on the internal balance at exactly 7 minutes from introduction time with space time 14-20 seconds in between them and the weight of the sample holder prior to being placed in the furnace is compared with the weight of the sample holder after it has been treated in the furnace to determine the amount of volatile material.

6 Claims, 3 Drawing Sheets

METHOD FOR AUTOMATIC THERMOGRAVIMETRIC VOLATILE ANALYSIS OF COAL AND COKE

BACKGROUND OF THE INVENTION

1. Field of the Invention

The present invention relates generally to an automatic method for ascertaining the volatile contents of coal samples. More particularly, this invention relates to a multiple sample precise method for accurately and automatically determining the volatile content of multiple coal or coke samples in sequence.

2. Description of Related Art

Coal is the most plentiful fuel in the fossil family. The use of coal increased dramatically in the $18^{th}$ century as the steam engine evolved and later as the use of electricity became common. Today the primary use of coal is to produce electrical energy. Coal is mined throughout many parts of the world; and thus, varied in its composition as mined. Since there are a wide variety of coals mined in different parts of the world, a coal may have a range of properties that differs from others, especially coals from diverse regions. A major factor in determining coal quality is coal rank. Coals ranked from lowest (brown coal) to highest (anthracite). The coal quality is determined by the amount of fixed carbon volatiles in the coal.

When coal is used in a power plant it is important to know the heat value of a coal by determining thermal weight losses due to the formation of volatile matter. Coal contains more than 50% by weight of carbon, and in high grade bituminous coal fixed carbon is 75-90%. The remainder is volatile matter which refers to other constituents of coal except moisture which are liberated at high temperatures. Volatile matter includes the products given off by a material as gas or vapor determined by prescribed methods, which determine the properties of coal.

A typical method of determining the volatiles in coal is through thermogravimetric analysis. In thermogravimetric analysis the mass of a sample in a rigidly controlled atmosphere is recorded as a function of temperature or time, or both. Each sample is subjected to a predetermined temperature and time and the measured weight loss determines the volatile matter content. Various methods for determining the volatile content through thermogravimetric analysis have been used. One method is ASTM standard designation D3175-11. D3175-11 it is manual method and its use is complex and slow. The precision of the results from using D3175-11 leaves a bias as to their accuracy as well as a desire to have a multiple sample analysis of coal samples. The manipulation is extensive and prone to errors. D3175-11 has the advantage that if done carefully and properly, results can be reproduced because the samples are always in same context, introduced in a hot furnace, other multiple sample ASTM method like D7582-10 ramps the furnace temperature from a lower temperature to temperature of 900-950 C. does not have the desired reproducibility because it is impossible to take the weights of all sample holders simultaneously to weight exactly at 7 minutes inside the furnace at furnace temperature of 950 C. for ASTM other temperatures for other standards as is required.

SUMMARY OF THE INVENTION

It is therefore the general object of the present invention to provide an automatic multiple sample reproducible method for accurately determining the value of volatiles in multiple samples of coal and coke by taking weights sequentially and exactly at 7 minutes+−1 second or better of furnace introduction.

This invention provides a method for the continuous thermogravimetric analysis of coal or coke for volatile matter in a thermogravimetric analyzer of the type including an auto-loading delivery system, a furnace, a movable platform within the furnace, an external balance and an internal balance for measuring the weight of a sample before and after treatment in the furnace. A coal or coke sample is placed in a sample holder. The sample holder is preferably a crucible made of platinum and having a lid but quartz crucible with lid will work as well.

A coal or coke sample of a predetermined known weight, preferably approximately 1 gram, is placed in the sample holder and weighed in the external balance with the lid in place. The sample holder containing the coal or coke sample is then auto-loaded into the hot furnace at 950 C. for ASTM other temperatures for other standards. Each sample holder is spaced approximately 14-20 seconds at introduction and the exact time of introduction recorded for each one. The 14-20 seconds' time space at introduction is used to allow each sample holder to be placed on top of the internal balance pedestal 3-4 seconds prior to the 7 minutes then at exactly the 7 minutes' time since introduction take the balance reading, then next sample will do same sequence. The furnace is heated to a predetermined temperature, preferably 950° C. for ASTM. The time inside the furnace must be exactly the same for each sample and it has been found that exactly 7 minutes is the most desirable. The sample holder is weighed on the internal balance (7 minutes exactly is preferred). The weight of the sample holder prior to placing it in the furnace is compared with the weight of the sample holder after it is heated in the furnace to determine the amount of volatile material in the coal sample.

The method of the present invention provides numerous advantages over the prior art as it provides the ability to accurately analyze and reproduce the amount of volatiles in a sample of coal or coke. When used with the analyzer disclosed herein the volatiles in a number of coal samples are continuously, automatically and accurately analyzed.

Other objects, features and advantages of the present invention will become apparent from the following detailed description of the invention taken in conjunction with the accompanying drawings.

BRIEF DESCRIPTION OF THE DRAWINGS

Having described the invention in general terms, reference will now be made to the accompanying drawings, which are not necessarily drawn to scale, and wherein.

DESCRIPTION OF THE PREFERRED EMBODIMENTS

Figure 1:
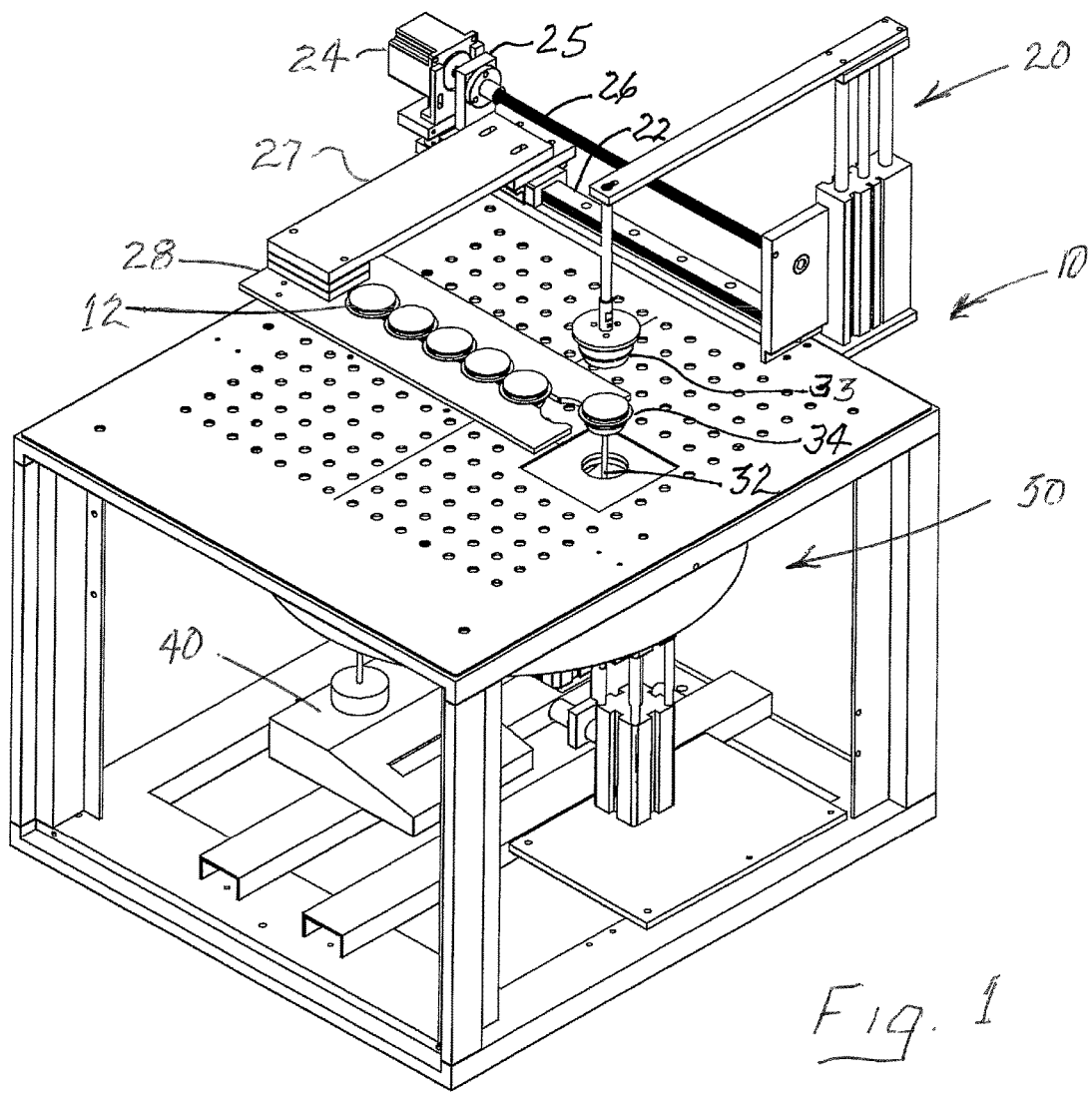
FIG. 1 is a perspective view of an analyzer of the type that may be used with the method of the present invention showing a deliver system for a linear auto-loader for loading samples to an analyzer furnace.

The present invention now will be described more fully hereinafter with reference to the accompanying drawings showing a preferred embodiment of an apparatus for use with the method of the invention. This invention may, however, be embodied in many different forms and should not be construed as limited to the embodiments set forth herein; rather these embodiments are provided so that this disclosure will be through and complete and will fully convey the scope of the invention to those skilled in the art. Like numbers refer to the elements throughout.

A method for continuous thermogravimetric analysis of coal or coke for volatile matter in a thermogravimetric analyzer of the type including an auto-loading delivery system, a furnace, a movable carousel within the furnace, an external balance and an internal balance for measuring the weight of a sample before and after treatment in the furnace.

To prepare the samples, each sample holder and lid is weighed on a balance or scale located outside the furnace to obtain tare weight. A predetermined weight of coal, preferably about one gram, to be analyzed is then placed in the sample holder and the sample holder with the material to be analyzed and cover is again weighed on the external balance. The external balance is connected to a recording system or computer which records the tare weight of each sample holder and the weight of the material to be analyzed for each sample holder. The sample holder is typically a crucible made of platinum and having a lid. It should be understood alternatively but less desirable, the sample holder may be made of nickel-chromium alloy or quartz.

The sample holder containing the coal sample with lid is placed in an opening in the auto-loader arm holder. The same procedure is repeated until the auto-loader is loaded. The sample holders will go inside the heated furnace automatically after the auto plug opens the furnace opening for insertion with at a predetermined interval, which may be approximately 14 seconds. This interval allows later positioning in the internal balance at the proper exact time of 7 minutes, this time of entrance inside the furnace is precisely measured. After all sample holders, lids and samples are inside the furnace, the plug will cover the furnace opening.

The furnace is heated at a predetermined temperature, preferably 950° C. for ASTM The time in the furnace must be same for each sample and it has been found that about 7 minutes exactly at 950° C. is the most desirable. The sample holder is weighed on the internal balance. The weight of the sample holder prior to placing it in the furnace is compared with the weight of the sample holder after it is heated in the furnace to determine the amount of volatile material in the coal sample. At exactly 7 minutes after insertion (of crucible number one) into the furnace minus 2-8 seconds the balance is tarred with no weight on balance then crucible is deposited on the balance and at exactly 7 minutes from insertion weight is taken. All crucibles with sample and lids are weighed exactly at 7 minutes from the insertion into the furnace. This is the volatile value as received, i.e., sample holder, lid, and sample original weight and subtracted from the value at exactly 7 minutes from insertion final total weight of the sample holder, lid and sample. Crucibles with samples and with lid are removed automatically to the auto loader for cooling. The furnace can operate with nitrogen or with air. It is activated automatically.

While the invention is directed to the method of analysis, set forth below is one example of a device for carrying out the method. There is shown in FIG. 1 an analyzer for use with the method of the present invention that includes an analyzer frame 10 whose major components are a linear auto-loading sample delivery system 20 and a furnace 30. The sample deliver system 20 includes auto-loader slider 22, driven by auto-loader motor 24 along driver screw 26. Connecting arm 27 is attached to slider in such manner that driver butt plate 25 will move arm 27 back and forth along the length of slider 22. Sample arm holder arm 28 has a series of openings along the length thereof sized to hold a crucible and is affixed to arm 27 and extends toward opening 36.

Figure 3:
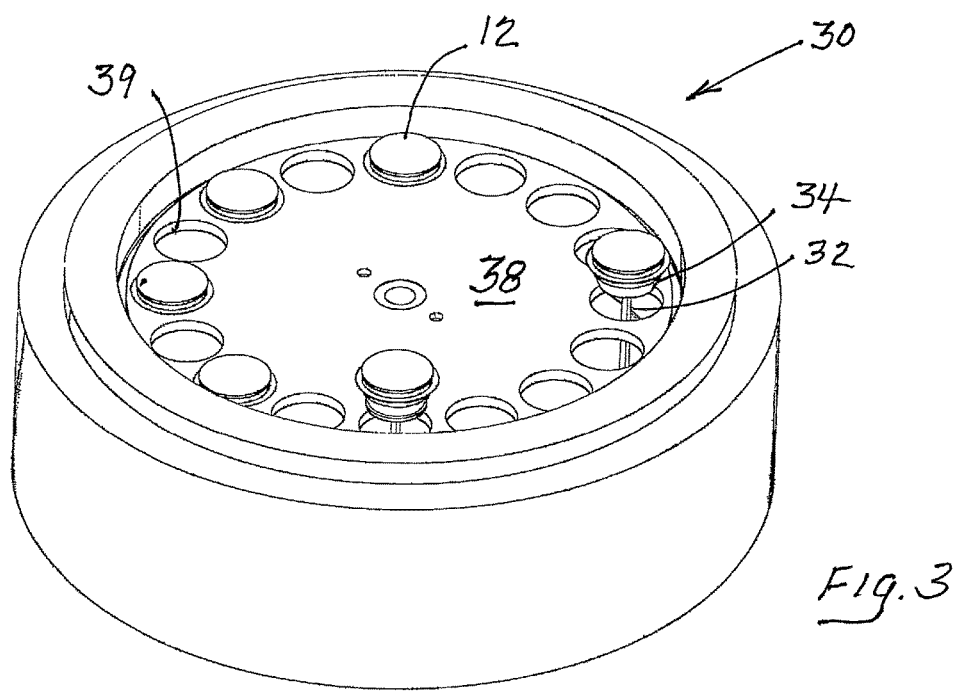
FIG. 3 is a perspective view of the internal carousel within the furnace and the placement of sample holders therein which may be used with the method of the present invention.
Figure 4:
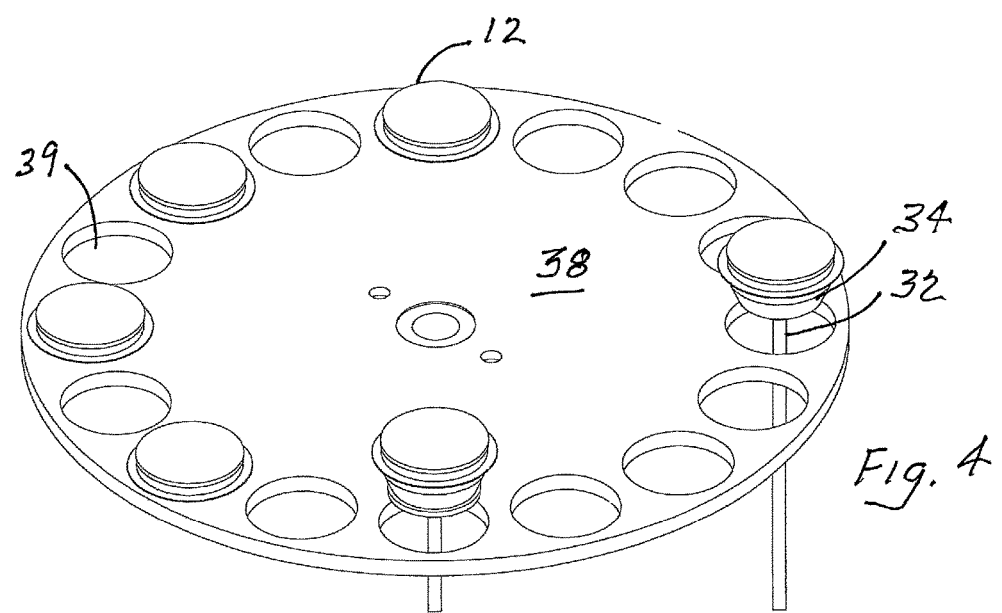
FIG. 4 is a perspective view of the internal carousel having sample holders placed therein that may be used with the method of the present invention.

The weighed sample holders 12 are transported by sample delivery system 20, one at a time, to internal carousel (a moveable platform) 38 (as shown in FIGS. 3 and 4) situated within the furnace 30. The furnace is heated to a predetermined temperature to exude the volatile contents of the sample. Transportation of the sample holders into the furnace is done by placing each of the weighed sample holders in a different one of the openings situated in crucible arm holder 28.

The crucible arm holder 28 and a movable ejector, together form an auto-loader mechanism. The ejector includes a vertically movable rod 32 and a pedestal 34. The auto-loader automatically places each sample holder 12 in turn into the furnace 30 through opening 36 in the top surface of the furnace. Furnace plug 33 is moved vertically to open and close furnace opening 36 to allow entry and exits of the weighed sample holders 12. The crucible arm holder 28 is moved linearly to place each sample holder in alignment with opening 36 in the top of furnace 30. The furnace chamber remains closed through all stages of the analysis such that no heat loss occurs and the furnace remains at a uniform temperature throughout the analysis.

Once the sample holder 12 is properly positioned relative to furnace opening 36, the vertically movable rod 32 and pedestal 34 are rise and pick up the sample holder from crucible arm holder 28. The sample holder is held above the plane of crucible arm holder 28 while the arm holder retracts thorough the operation of the linear slider 22. The ejector pedestal 34 then moves down through furnace opening 36 in the top of furnace 30, placing the sample holder within the furnace.

Figure 2:
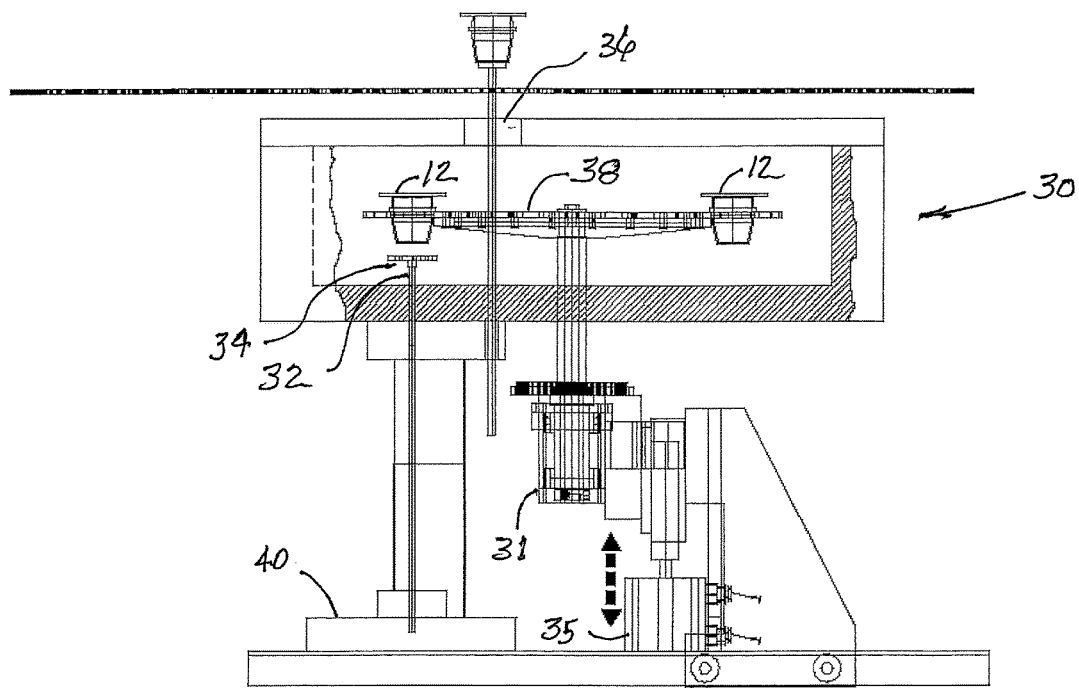
FIG. 2 is a side cross-sectional view of the inside of an analyzer furnace used with the method of the present invention showing the internal carousel and sample holders placed in the carousel.

As shown in FIG. 2, the sample holder 12 is placed on a rotatable carousel 38 situated in the furnace. Carousel 38 can rotate and can move up and down along its central axis. As shown in FIGS. 3 and 4, the carousel 38 has a series of spaced apertures 39 around its periphery. Apertures 39 are adapted to retain sample holders 12 and to suspend the sample holders within the furnace during analysis. The opening 36 in the top surface of the furnace 30 is positioned such that when carousel 38 comes into position for loading or unloading, one of the apertures 39 in the carousel is aligned with opening 36 in the top of the furnace.

The furnace 30 is heated to the predetermined temperature before the sample holders; each having a sample of known weight are loaded into it. While within the furnace, situated on the carousel 38, the sample holders are heated for a predetermined time. At appropriate points in the testing cycle, carousel 38 is rotationally indexed by a motor 31 such that the sample holders are each in turn aligned with and automatically deposited on a pedestal 34 attached on the end of an upstanding rod 32 associated with an internal balance 40 through vertical motion of the internal carousel. As shown in FIG. 2, a pneumatic cylinder 35 acts to raise and lower carousel 38 to enable the sample holders to be deposited and removed from pedestal 34 of weighing platform of internal balance 40. The weight of each sample holder is recorded and compared during the test cycle.

After weighing, the weighed sample holder is placed back on carousel 38. Carousel 38 is indexed and the next sample holder in turn is weighed. The internal balance 40 is connected to a recording system or computer which records data reflecting the difference between the weight of the sample holder as determined by the external balance prior to transporting the sample holder into the furnace and the weight of the sample holder as determined by the internal balance after the weighing of that sample holder.

Once the weighing in the test cycle is performed for all particular sample holders, the sample holders are removed sequentially through opening 36 on the upper surface of the furnace 30 by the same auto-loader mechanism that was used to introduce them; crucible holder arm 28 and ejector pedestal 34. The sample holders are allowed to cool, after which the samples are removed from the sample holder, sample holder cleaned and reused.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for determining the volatile content of samples of coal and or coke in a thermogravimetric analyzer of the type including a hot furnace, and a movable platform within said furnace, said thermogravimetric analyzer being associated with an external balance, and an internal balance, said method comprising the steps of:
    (a) weighing multiple sample holders having a lid and a predetermined amount of a coal or coke sample in said external balance;
    (b) placing sequentially said sample holders in external furnace auto loader;
    (c) introducing the sample holders automatically with a time space for each of approximately 14-20 seconds for each sample holder to allow exact sequential weighing later inside the furnace;
    (d) closing a furnace plug after all sample holders are introduced;
    (e) maintaining a furnace temperature at said sample holders in said hot furnace at a predetermined temperature for a predetermined exact time;
    (f) sequentially weighing all sample holders on said internal balance with a time space each of approximately 14-20 seconds each to allow exact sequential weighing of all of them at predetermined time of 7 minutes from furnace introduction; and
    (g) comparing the weight of the sample holder prior to placing the sample holder into the furnace with the weight of the sample holder after the sample holder has been heated in the furnace for an exact time to determine the amount of volatile material in said coal or coke samples.

2. The method of claim 1, wherein said furnace is heated at a temperature of 950° C. for ASTM other temperatures for other standards will work exactly the same.

3. The method of claim 1, wherein the amount of said coal sample is approximately 1 gram.

4. The method of claim 1, wherein the time of heating is seven minutes.

5. The method of claim 1, wherein said method is performed continuously on a number of coal samples.

6. A continuous method for multiple sample thermogravimetric analysis of coal or coke for volatile matter in a thermogravimetric analyzer of the type including a linear auto-loader, a furnace, and a movable platform within said furnace, said thermogravimetric analyzer being associated with an external balance and an internal balance, the method comprising:
    (a) weighing a sample holder having a lid and a coal or coke sample in said external balance;
    (b) auto-loading said sample holder containing said coal or coke samples into said furnace;
    (c) keeping said sample holder in said furnace at a temperature of 950° C for exactly 7 minutes before taking its weight;
    (d) weighing said heated sample holder and sample from step (c) on said internal balance while at said temperature; and
    (e) comparing the weight of said sample holder, lid, and sample prior to placing the sample holder, lid, and sample into the furnace with the weight of the sample holder, lid, and sample after the sample has been heated in the furnace to determine the amount of volatile material in said coal sample.

* * * * *